US009600629B2

United States Patent
Allen et al.

(10) Patent No.: US 9,600,629 B2
(45) Date of Patent: *Mar. 21, 2017

(54) SECURING PROTECTED HEALTH INFORMATION BASED ON SOFTWARE DESIGNATION

(71) Applicant: International Business Machines Corporation, Armonk, NY (US)

(72) Inventors: Corville O. Allen, Morrisville, NC (US); Lee N. Helgeson, Rochester, MN (US); Russel L. Young, Rochester, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,174

(22) Filed: Jun. 24, 2015

(65) Prior Publication Data
US 2016/0283663 A1    Sep. 29, 2016

Related U.S. Application Data

(63) Continuation of application No. 14/667,908, filed on Mar. 25, 2015.

(51) Int. Cl.
*G06F 12/14*    (2006.01)
*G06F 17/30*    (2006.01)
(Continued)

(52) U.S. Cl.
CPC .......... *G06F 19/322* (2013.01); *G06F 3/0622* (2013.01); *G06F 3/0637* (2013.01);
(Continued)

(58) Field of Classification Search
CPC ............... G06F 9/45558; G06F 19/322; G06F 12/1491; G06F 12/08; G06F 21/6209;
(Continued)

(56) References Cited

U.S. PATENT DOCUMENTS 5,845,129 A * 12/1998 Wendorf ............. G06F 12/1491
710/200
7,293,142 B1 * 11/2007 Xu ...................... G06F 11/3648
707/999.202

(Continued)

OTHER PUBLICATIONS

Efstathopoulos, Petros, et al. "Labels and event processes in the Asbestos operating system." ACM SIGOPS Operating Systems Review. vol. 39. No. 5. ACM, 2005.*

(Continued)

*Primary Examiner* — Michael Simitoski
(74) *Attorney, Agent, or Firm* — Patterson + Sheridan, LLP

(57) ABSTRACT

Methods to perform an operation comprising receiving, from a first process, a request to access content stored in a memory, determining that the content comprises protected health information (PHI), determining, from a secure table, a set of processes permitted to access the PHI, upon determining the first process is not a member of the set of processes, restricting access to the PHI by the first process, and upon determining the first process is a member of the set of processes, permitting access to the PHI by the first process.

6 Claims, 3 Drawing Sheets

(51) Int. Cl.
*G06F 19/00* (2011.01)
*G06F 11/07* (2006.01)
*G06F 3/06* (2006.01)
*G06F 9/455* (2006.01)
*G06F 21/62* (2013.01)
*G06F 21/00* (2013.01)

(52) U.S. Cl.
CPC ........ *G06F 3/0673* (2013.01); *G06F 9/45558* (2013.01); *G06F 11/073* (2013.01); *G06F 11/0751* (2013.01); *G06F 11/0778* (2013.01); *G06F 21/6245* (2013.01); *G06F 2009/45587* (2013.01)

(58) Field of Classification Search
CPC ............. G06F 21/6218; G06F 21/6227; G06F 2221/2141; G06F 12/14; G06F 12/1483; G06F 21/6245; G06F 2221/2113; G06F 11/073; G06F 11/0751; G06F 11/0778; G06F 3/0622; G06F 3/0637; G06F 3/0673; G06F 2009/45587; H04L 63/105
See application file for complete search history.

(56) References Cited

U.S. PATENT DOCUMENTS

| | | | | |
|---|---|---|---|---|
| 8,850,057 | B2 | 9/2014 | Natoli et al. | |
| 2003/0079103 | A1* | 4/2003 | Morrow | G06F 12/1027 711/206 |
| 2004/0010701 | A1* | 1/2004 | Umebayashi | G06F 21/6227 713/193 |
| 2004/0030912 | A1* | 2/2004 | Merkle, Jr. | G06F 21/10 726/26 |
| 2004/0172558 | A1 | 9/2004 | Callahan et al. | |
| 2004/0187020 | A1* | 9/2004 | Leerssen | H04L 63/105 713/166 |
| 2005/0062603 | A1 | 3/2005 | Fuerst et al. | |
| 2006/0265375 | A1* | 11/2006 | Hess | G06F 21/6227 |
| 2007/0050580 | A1* | 3/2007 | Lewis | G06F 12/1483 711/163 |
| 2007/0113266 | A1* | 5/2007 | Ross | G06F 21/10 726/1 |
| 2007/0255912 | A1* | 11/2007 | Kelly | G06F 21/6245 711/159 |
| 2007/0300299 | A1 | 12/2007 | Zimmer et al. | |
| 2008/0244206 | A1* | 10/2008 | Heo | G06F 12/1491 711/163 |
| 2009/0007233 | A1* | 1/2009 | Smith | G06F 21/6218 726/2 |
| 2009/0328129 | A1* | 12/2009 | Desai | G06F 21/6209 726/1 |
| 2011/0289294 | A1* | 11/2011 | Maeda | G06F 21/74 711/163 |
| 2014/0115652 | A1* | 4/2014 | Kapoor | G06F 21/554 726/1 |
| 2014/0257047 | A1 | 9/2014 | Sillay et al. | |
| 2015/0301952 | A1* | 10/2015 | McKinley | G06F 12/08 711/207 |

OTHER PUBLICATIONS

Dai Zovi, Dino A. "Apple iOS 4 security evaluation." Black Hat USA (2011): 1-29.*
Robinson, Jeffrey D. "Beyond the DICOM Header: Additional Issues in Deidentification." American Journal of Roentgenology 203.6 (2014): W658-W664.*
Yang, Jisoo, and Kang G. Shin. "Using hypervisor to provide data secrecy for user applications on a per-page basis." Proceedings of the fourth ACM SIGPLAN/SIGOPS international conference on Virtual execution environments. ACM, 2008.*
Cheng et al. "Abstractions for Usable Information Flow Control in Aeolus", USENIX Annual Technical Conference 2012, 13 pages.
Liu et al. "Strengthening Legal Compliance for Privacy in Electronic Health Information Systems: A Review and Analysis", Proceedings of the National e-Health Privacy and Security Symposium 2006 (ehPASS'06)—ISBN:1741071380, (2006) pp. 51-66.
Petkovic et al., "Rights Management Technologies: A Good Choice for Securing Electronic Health Records?", ISSE/SECURE 2007 Securing Electronic Business Processes, Vieweg 2007 pp. 178-187.
Luethi et al., "Security in Health Information Systems: An Exploratory Comparison of U.S. and Swiss Hospitals", Proceedings of the 42nd Hawaii International Conference on System Sciences—2009, IEEE 2009.
Allen et al., "Securing Protected Health Information Based on Software Designation", U.S. Appl. No. 14/667,908, filed Mar. 25, 2015.
2015 IBM "List of IBM Patents or Patent Applications Treated as Related", 2015.

* cited by examiner

SECURING PROTECTED HEALTH INFORMATION BASED ON SOFTWARE DESIGNATION

CROSS-REFERENCE TO RELATED APPLICATION

This application is a continuation of co-pending U.S. patent application Ser. No. 14/667,908, filed Mar. 25, 2015. The aforementioned related patent application is herein incorporated by reference in its entirety.

BACKGROUND

The present invention relates to securing protected health information (PHI) data, and more specifically, to securing protected PHI data based on a software designation.

The Health Insurance Portability and Accountability Act (HIPAA) requires that health information remain protected and confidential when stored in computer systems. However, such personal information may be susceptible to exposure under certain circumstances. For example, when an operating system experiences a failure, a mechanism is used to collect data from the computer's memory to help assist in troubleshooting and repair processes. Similarly, a program that crashes or otherwise fails may send crash-related data that can be stored in memory. If the memory includes protected health information, the data dump could violate the privacy requirements of HIPAA.

SUMMARY

Embodiments disclosed herein provide systems, methods, and computer program products to perform an operation comprising receiving, from a first process, a request to access content stored in a memory, determining that the content comprises protected health information (PHI), determining, from a secure table, a set of processes permitted to access the PHI, upon determining the first process is not a member of the set of processes, restricting access to the PHI by the first process, and upon determining the first process is a member of the set of processes, permitting access to the PHI by the first process.

DETAILED DESCRIPTION

Embodiments disclosed herein provide techniques to secure sensitive data. Embodiments disclosed herein allow software processes executing on a computer to specify, in a secure profile, whether the software uses, accesses, writes, or otherwise interacts with protected health information (PHI). A management entity, such as an operating system or hypervisor, may manage the secure profile. When a process associated with PHI data attempts to write to memory or storage, the operating system (or hypervisor) may mark the data as protected (or secure) PHI data in the secure profile. The operating system (or hypervisor) must then authorize subsequent attempts to access the PHI data made by any process. The management entity prevents processes unauthorized processes from accessing the PHI data.

For example, in the event of a system failure, a memory dump process may be initiated to collect information stored in memory. The memory dump may be a snapshot of system memory (or the memory allocated to a virtual machine). However, the memory may contain PHI data, such as in the case where database tables are pre-loaded into memory for performance reasons. If the memory contains PHI data, embodiments disclosed herein may restrict the memory dump process from reading the PHI data, keeping the PHI data secure. Similar techniques may be applied to other scenarios, such as where an application crashes, and the contents of memory are sent to a remote source (such as the developer of the application) as part of a reporting feature provided by developer.

Similarly, in virtualized environments, virtualization/partition platform dump may occur in the event of a failure. Such memory dumps may include large amounts of customer data spanning multiple domains (such as memory and processors). This data may be used by the virtual host (such as a hypervisor) to manage resources from pooled resources (such as memory, processors, and disk I/O). With the advent of virtualized technologies such as hibernation and suspension of virtual machines, the hypervisor may have customer data preserved in its memory due to the requirements to be able to resume the virtual machine at any given time. Similarly, if a problem occurs in the system while the data is in the memory, a dump of the host machine will include personal data, such as PHI data. Embodiments disclosed herein ensure that any such data is accessible only to a finite set of pre-approved software processes.

Although protected health information (PHI) data is used as a reference example herein, the disclosure is equally applicable to securing all types of data, and any reference to PHI data should not be considered limiting of the disclosure. Similarly, the use of "software," "process," or "service" should not be considered limiting of the disclosure, as embodiments disclosed herein apply to other applications or code attempting to access secure data.

Figure 1:
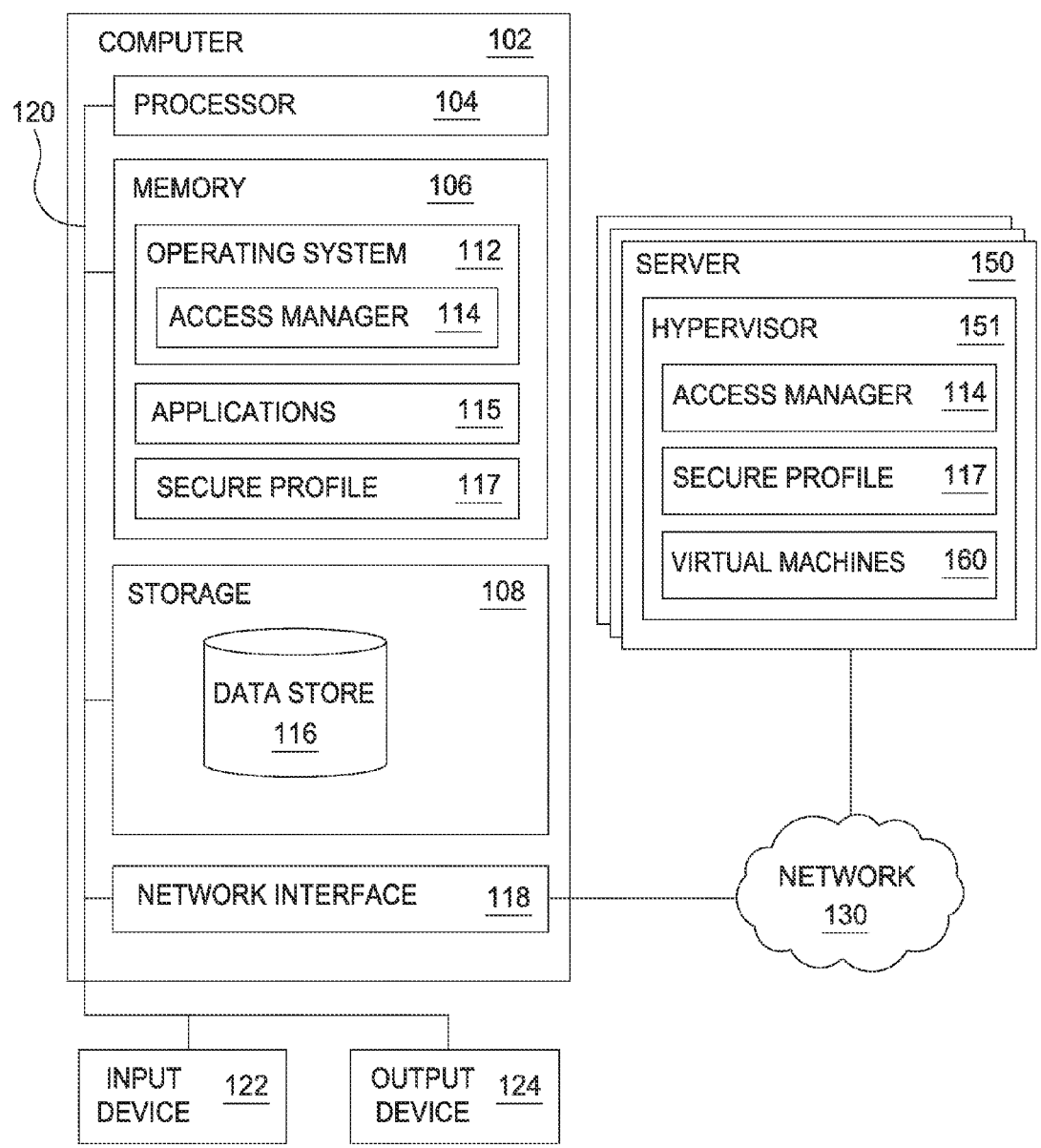
FIG. 1 illustrates a system which secures protected PHI data based on a software designation, according to one embodiment.

FIG. 1 illustrates a system 100 which a system which secures protected PHI data based on a software designation, according to one embodiment. The system 100 includes a computer 102 connected to other computers via a network 130. In general, the network 130 may be a telecommunications network and/or a wide area network (WAN). In a particular embodiment, the network 130 includes access to the Internet.

The computer 102 generally includes a processor 104 which obtains instructions and data via a bus 120 from a memory 106 and/or storage 108. The computer 102 may also include one or more network interface devices 118, input devices 122, and output devices 124 connected to the bus 120. The computer 102 is generally under the control of an operating system 112. Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 104 is a programmable logic device that performs instruction, logic, and mathematical processing, and may be representative of one or more CPUs. The network interface device 118 may be any type of network communications device allowing the computer 102 to communicate with other computers via the network 130.

The storage 108 is representative of hard-disk drives, solid state drives, flash memory devices, optical media and the like. Generally, the storage 108 stores application programs and data for use by the computer 102. In addition, the memory 106 and the storage 108 may be considered to include memory physically located elsewhere; for example, on another computer coupled to the computer 102 via the bus 120.

The input device 122 may be any device for providing input to the computer 102. For example, a keyboard and/or a mouse may be used. The input device 122 represents a wide variety of input devices, including keyboards, mice, controllers, and so on.

As shown, the memory 106 contains the operating system 112, an access manager 114, an application 115, and a secure profile 117. The access manager 114 is an application generally configured to control access to secure data, such as PHI data. Although shown as a component of the operating system 112, the access manager 114 may execute as a standalone application, process, or service that interacts with the operating system 112. Generally, the access manager 114 maintains the secure profile 117 to facilitate fulfillment (or restriction) of attempts to access PHI data by an application 115. When an application 115 writes PHI data to the memory 106 (and/or the storage 108), the application 115 or the access manager 114 may update the secure profile 117 to reflect that the memory location includes PHI data. The secure profile 117 may include an indication of the owner (or generator) of the PHI data and a set of entities (such as other applications 115, software processes, or services) permitted to access the PHI data. When software attempts to access the PHI data, the access manager 114 may reference the secure profile 117 to determine whether the requesting software entity is permitted to access the PHI data. If the requesting entity is not specified in the set of entities, the access manager 114 (and/or the operating system 112) may restrict access to the PHI data. If, however, the requesting entity is specified in the permitted set of entities, the access manager 114 (and/or the operating system 112) may allow access to the PHI data.

The applications 115 may be any type of executable software, such as applications, services, and processes. The secure profile 117 is a data structure configured to hold information reflecting which software created data (stored in the memory 106 and/or the storage 108), whether the data is PHI data, and any software entities that can access the PHI data. In another embodiment, the secure profile 117 may specify precise locations in the memory 106 and/or storage 108 that include PHI data. Although reflected as being stored in the memory 106, the secure profile 117 may be stored in any feasible location, including the storage 108. As shown, the storage 108 includes a data store 116. The data store 116 may include any type of data, including PHI data.

As shown, the networked system 100 includes a plurality of servers 150. The servers 150 execute hypervisors 151 which create, run, and manage virtual machines 160. The virtual machines 160 may provide services (not pictured) that create PHI data. Therefore, in one embodiment, the hypervisor 151 includes (or interacts with) instances of the access manager 114 and the secure profile 117. As described above, doing so secures sensitive PHI information stored in a memory or storage accessible to the server 150 (or software executing thereon).

Figure 2:
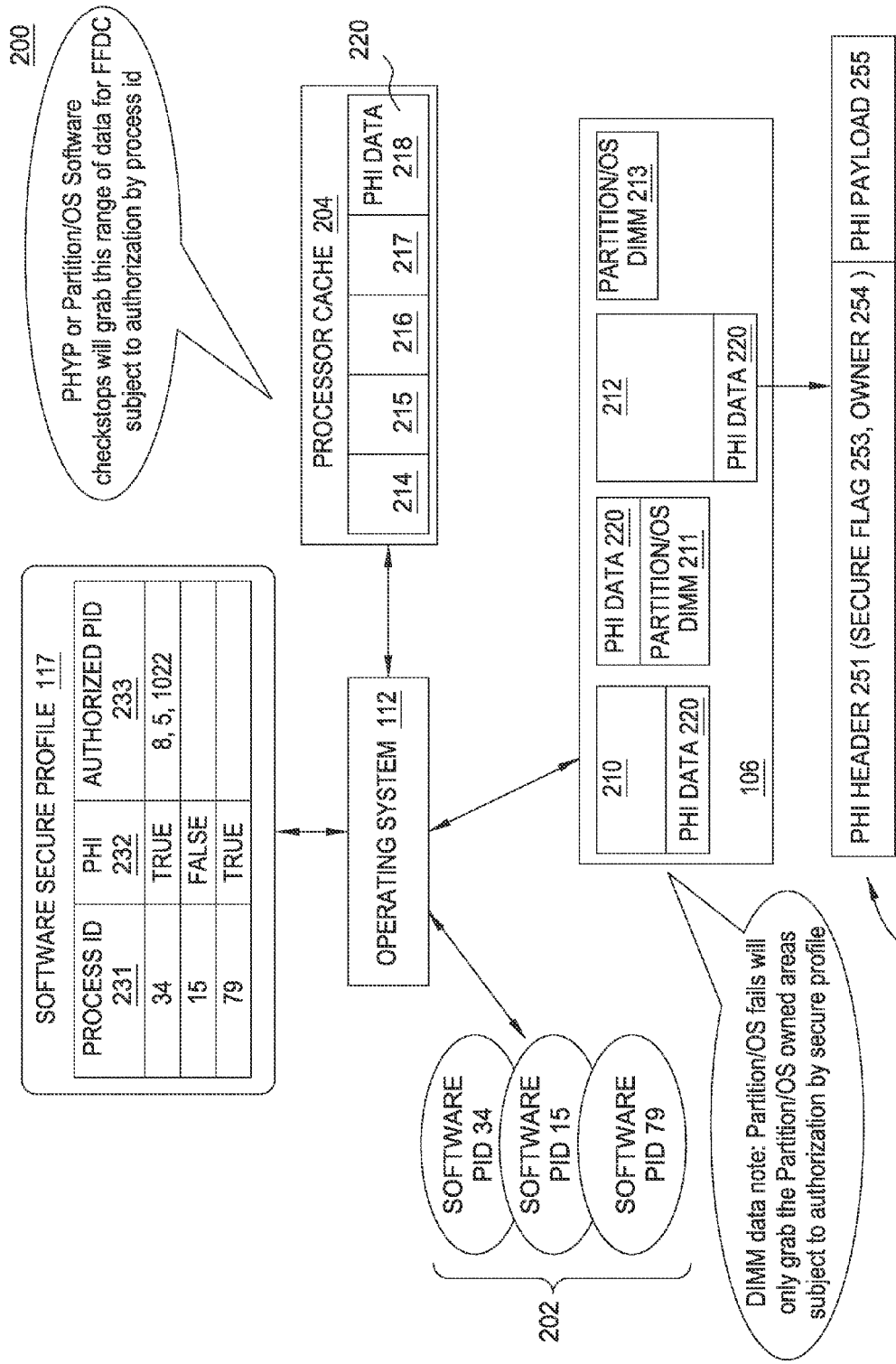
FIG. 2 illustrates techniques to secure protected PHI data based on a software designation, according to one embodiment.

FIG. 2 is a schematic diagram 200 illustrating techniques to secure protected PHI data based on a software designation, according to one embodiment. That is, the schematic diagram 200 illustrates an embodiment where the operating system 112 orchestrates the implementation of a secure profile 117 to protect secure data, such as PHI data. In other embodiments, a hypervisor may perform the functionality of the operating system (OS) 112. As shown, a plurality of software processes 202 may interact with the OS 112 during execution. During execution, the software processes 202 may generate, write, access, or otherwise use data in the processor cache 204, memory 106, or other storage such as hard drives (not pictured). The processes 202 may be any executable software, and three example processes 202 are shown. The processes 202 are uniquely identified by one or more process identifiers (PID), such as the depicted PIDs of 15, 34, and 79. Generally, the software processes 202 may be identified by any suitable identifier. When one of the software processes 202 writes data to a storage location, the OS 112 (or a component thereof, such as the access manager 114) may update the secure profile 117 accordingly. Specifically, the processes 202 may inform the operating system 112 that they generate, write, use, or otherwise access PHI data. In one embodiment, the processes 202 may initially register with the OS 112 as being associated with PHI data. In another embodiment, the processes 202 may inform the OS 112 that PHI data is being written to storage with each write (or other data access operation).

As shown, the operating system 112 has populated the secure profile 117 with data. Specifically, the secure profile 117 includes a process ID field 231, a PHI flag 232, and a set of process IDs 233. The process ID field 231 is an identifier of the processes 202. The PHI flag 232 indicates whether the process 202 having the process ID 231 is associated with PHI data. The authorized PIDs 233 indicate whether other processes 202 are authorized to access the PHI data created by the process 202 having the process ID 231. Therefore, as shown, the secure profile 117 indicates that process ID 34 is associated with PHI data, and that processes having a process ID of 8, 5, and 1022 are authorized to access the PHI data generated or owned by the process 202 having a process ID of 34. Furthermore, as shown, the secure profile 117 reflects that process ID 15 is not associated with PHI data, and process ID 79 is associated with PHI data, but no additional processes are authorized to access the PHI data owned or generated by process ID 79.

When one of the processes 202 writes PHI data to the processor cache 204 or memory 106, the operating system 112 may mark the data as such. As shown, therefore, the memory location 218 in the processor cache 204 is defined as holding PHI data 220, while memory locations 214-217 are not associated with PHI data. Similarly, as shown, the memory 106 includes a plurality of physical memory units 210-213. The OS 112 has marked regions of memory units 210, 211, and 212 as holding PHI data 220, while memory unit 213 is not storing PHI data. As shown in FIG. 2, a detailed view 250 of the PHI data 220 describes the content of the PHI data 220. Specifically, the detailed view 250 shows that the PHI data 220 includes a PHI header 251 and a PHI payload portion 255. The PHI payload 255 is the data portion of the PHI data 220—it is the payload 255 that includes the protected information. As shown, the PHI header 251 includes a secure flag 253 and an owner field 254. The secure flag 253 of the PHI header 251 specifies whether the data is secure data, such as PHI data. The owner field 254 of the PHI header 251 is configured to store the process ID 231 of a process 202. Therefore, the owner field 254 and secure flag 253 of the PHI header 251 may correspond to the process ID 231 and secure flag 232 of the software secure profile 117, respectively. For example, a first PHI header 251 may specify a secure flag 253 of "true" and an owner field 254 of "34," indicating the PHI data 220 stored in the memory 212 is secure data owned by the process 202 having a process ID of 34. In at least one embodiment, the PHI header 251 may also specify additional processes permitted to access the PHI data (such as the processes defined in the authorized PID 233).

When another process 202 attempts to access data, the OS 112 may determine, from the PHI header 251, whether the data is secure PHI data. If the secure flag 253 of the PHI header 251 indicates the data is secure PHI data 220, the OS 251 may use the owner field 254 from the PHI header 251 to determine whether to grant access to the PHI data 220. For example, if the process ID of the process 202 matches the owner field 254 of the PHI header 251, the OS 112 may permit access to the PHI data 220. However, if the process ID does not match the owner field 254 of the PHI header 251, the OS 112 may index the secure profile 117 using the owner field 254 as a process ID 231, and determine whether the process ID attempting to access the PHI data 220 is listed as a member of the set of PIDs 233 authorized to access the PHI data 220. If the process requesting access to the PHI data 220 is an authorized process in the authorized PIDs 233, the OS 112 may permit access to the PHI data 220. If the process requesting access to the PHI data 220 is not an authorized process, the OS may restrict access to the PHI data 220.

Therefore, for example, if the PHI data 220 in the memory 210 has a PHI header 250 specifying a secure flag 253 of "true" and an owner flag 254 of "34," and process 34 subsequently requests access the PHI data 220 in the memory 210, the OS 112 may permit the process 34 to access the PHI data 220, as process 34 is the owner of the PHI data. Similarly, if process 1022 attempts to access the PHI data 220 in memory 210 owned by process 34, the OS 112 may permit access, as process 1022 is listed as an authorized PID 233 in the secure profile 117. If, however, process 15 attempts to access the PHI data 220 in memory 210 owned by the process 34, the OS 112 may block the access, as the process 15 is not the owner of the data, and is not listed as authorized in the authorized PIDs 233 for process ID 34. If data stored in the system has a header 251 with a secure flag 253 that indicates the data is not secure, then any process 202 may access the data.

As another example, if the process 15 is a memory dump process configured to read and output the data in the processor cache 204 and/or the memory 106, the process 15 will not output secure PHI data 220. Because process 15 is not listed as being an owner 254 of PHI data in any PHI header 251, and process 15 is not an authorized PID 233 for any PHI data in the secure table 117, the process 15 cannot read the PHI data 220.

Figure 3:
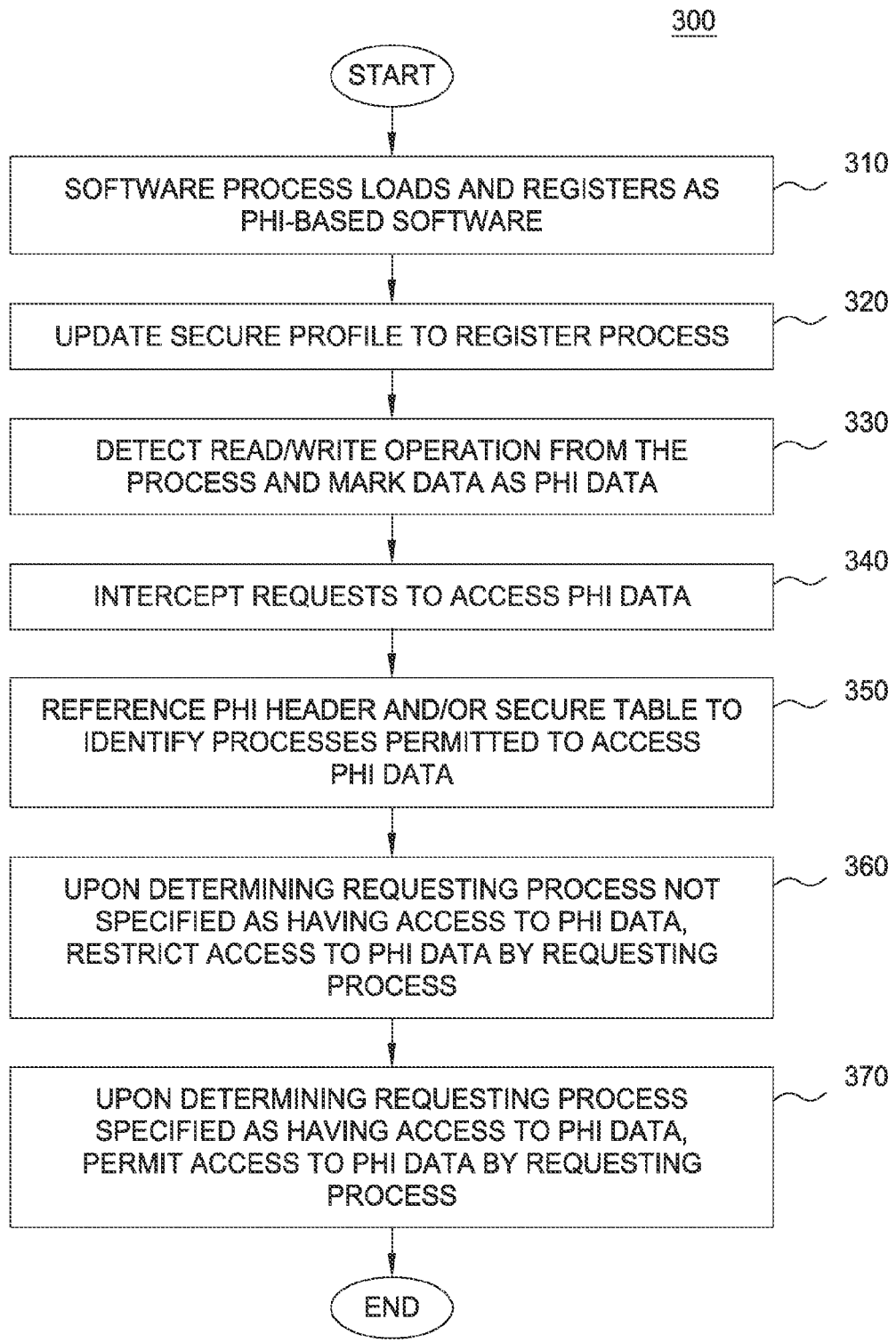
FIG. 3 illustrates a method to secure protected PHI data based on a software designation, according to one embodiment.

FIG. 3 illustrates a method 300 to secure protected PHI data based on a software designation, according to one embodiment. Generally, the steps of the method 300 ensure that data designated as protected data is only accessible to authorized software processes. The method 300 begins at step 310, where a software process loads and executes on a computing system, and registers itself as PHI-based software with the operating system (OS) 112 and/or the access manager 114. The software process may be any executable computer code, such as an application, executable, driver, service, and the like. At step 320, the OS 112 may update the secure profile 117 to include a process ID 231 for the registering process and an authorized PID 233 of any other processes the registering process indicates are authorized to access PHI data generated by the registering process.

At step 330, the OS 112 may detect read and/or write operations performed by the registered process to storage (such as memory, caches, registers, and/or secondary storage), and mark the subject data as PHI data. For example, if the registered process saves a file to a hard drive, the OS 112 may add a PHI header to the file indicating the file includes PHI data and is owned by the registered process. Similarly, if the registered process writes data to the system's L1 cache, the OS 112 may add a PHI header to the data indicating the data includes PHI data and is owned by the registered process. At step 340, the OS 112 may intercept a request to access data that has been marked as PHI data. The access may be any operation, such as a read, write, modify, or deletion operation. The request may be made by any process executing on the system. The OS 112 may determine that the request targets PHI data based on the PHI header associated with the requested data. At step 350, the OS 112 may reference the PHI header of the data and/or the secure table 117 to determine whether the requesting process has the requisite permissions to access the data. For example, if the requesting process is the owner (or creator) of the PHI data, the process ID listed as owner in the PHI header for the PHI data would match the process ID of the requesting process, and the OS 112 would permit access to the data. If the requesting process is not the owner (or creator) of the PHI data, the OS 112 may reference the secure table 117 to determine whether the process ID of the process is specified as an authorized PID 233 for the PHI data.

At step 360, the OS 112 may restrict the requesting process from accessing the PHI data upon determining that the requesting process does not have permission to access the PHI data. For example, the OS 112 may determine that the requesting process is not the owner of the data (as specified in the PHI header) and determine that the requesting process is not listed as an authorized process 233 in the secure table 117. At step 370, the OS 112 may permit the requesting process's request to access the PHI data upon determining that the process is permitted to access the PHI data. For example, the OS 112 may determine that the requesting process is specified as the owner of the data in the PHI header of the PHI data. Similarly, the OS 112 may determine that the secure table 117 entry associated with the PHI data includes the requesting process as a member of the authorized processes 233.

Advantageously, embodiments disclosed herein provide techniques to maintain the security of personal health information stored in computer storage. Embodiments disclosed herein mark stored data containing such information as PHI data, and maintain a secure table specifying software modules permitted to access the PHI data. Doing so keeps the PHI data secure, as current processes may unknowingly expose the PHI data during normal operation.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the foregoing, reference is made to embodiments presented in this disclosure. However, the scope of the present disclosure is not limited to specific described embodiments. Instead, any combination of the recited features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the recited aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. For example, the access manager 114 could execute on a computing system in the cloud and restrict access to PHI data based on software profiles. In such a case, the access manager 114 could maintain a data store listing permissions to access PHI data at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
receiving, from a first process, a request to access content stored in a memory;
determining that the content comprises protected health information (PHI), wherein the PHI comprises: (i) a header portion and (ii) a data portion, wherein the header portion comprises: (i) an indication that the PHI is secure data, and (ii) an indication of an owner process that created the PHI data;
determining, from a secure table stored in the memory and from the header portion, a set of processes permitted to access the PHI;
upon determining the first process is not a member of the set of processes, restricting the first process from accessing the PHI; and
upon determining the first process is a member of the set of processes, permitting the first process to access to the PHI.

2. The method of claim 1, further comprising:
prior to receiving the request:
writing the PHI data to the memory; and
writing, to the secure table, an indication: (i) of the owner process writing the PHI data, (ii) that the PHI data is secure data, and (iii) the set of processes permitted to access the PHI.

3. The method of claim 2, wherein the first process comprises the owner process, wherein the first process is permitted to access the PHI.

4. The method of claim 1, wherein the request is part of a memory dump performed by the first process responsive to a system failure, wherein the memory dump does not include the PHI data, wherein the first process is not a member of the set of processes, wherein the first process did not write the PHI data to the memory.

5. The method of claim 1, wherein the request is received by at least one of: (i) an operating system, and (ii) a hypervisor, wherein the at least one of the operating system and the hypervisor restricts access to the PHI by the first process, wherein the at least one of the operating system and the hypervisor permits access to the PHI by the first process.

6. The method of claim 1, wherein the content is determined to comprise PHI data based on at least one of: (i) the header portion of the PHI, and (ii) the secure table, wherein the header portion of the PHI further comprises an indication of the set of processes permitted to access the PHI.

* * * * *